United States Patent [19]

Sankey et al.

[11] Patent Number: 4,920,207

[45] Date of Patent: Apr. 24, 1990

[54] SELECTED REMOVAL OF TRITYL GROUPS FROM TRISPA

[75] Inventors: George H. Sankey; Nigel J. Homer, both of Reading, Great Britain

[73] Assignee: Tate & Lyle Public Ltd. Co., United Kingdom

[21] Appl. No.: 98,023

[22] Filed: Sep. 17, 1987

[30] Foreign Application Priority Data

Sep. 17, 1986 [GB] United Kingdom ............... 8622342

[51] Int. Cl.$^5$ .................... C07H 1/00; C07H 5/02; C07H 13/02

[52] U.S. Cl. .................... 536/124; 536/125; 536/122; 536/18.4; 536/18.5

[58] Field of Search .................. 536/122, 125, 124

[56] References Cited

U.S. PATENT DOCUMENTS 4,362,869  12/1982  Jenner et al. ................. 536/122
4,801,700  1/1989   Tully et al. .................. 536/125

OTHER PUBLICATIONS

Rao, Vanga S. and Arthur S. Perlin (1980), "Removal of O–benzyl Protecting-groups or Carbohydrate Derivatives by Catalytic; Transfer Hydrogenation", Carbo. Res. 83:175–7.

R. L. Augustine, *Catalytic Hydrogenation*, Marcel Dekker, New York, 1965, 125, 135–137.

W. H. Hartung and R. Simonoff *Organic Reactions*, 7, 263 (1953).

McKeown et al., Canadian Journal of Chemistry, 35, 28–36, 1957.

*Primary Examiner*—Johnnie R. Brown
*Assistant Examiner*—Gary L. Kunz
*Attorney, Agent, or Firm*—Ostrolenk, Faber, Gerb & Soffen

[57] ABSTRACT

2,3,4,3',4'-penta-O-acetyl sucrose (4-PAS), a key intermediate in the preparation of sucralose, is prepared by the selective removal of trityl groups from 6,1',6'-tri-O-trityl-penta-O-acetyl sucrose (TRISPA) in which a catalytic amount of an aralkyl chloride or hydrogen chloride is added to a solution of TRISPA is an inert organic solvent is hydrogenated in the presence of a hydrogenolysis catalyst such a platinum or palladium.

13 Claims, No Drawings

SELECTED REMOVAL OF TRITYL GROUPS FROM TRISPA

This invention relates to an improved process for the preparation of 2,3,4,3',4'-penta-O-acetyl sucrose ("4-PAS") and hence, the preparation of its isomer 2,3,6,3',4'-penta-O-acetyl sucrose ("6-PAS") which is an intermediate in the synthesis of the high intensity sweetener, sucralose (4,1',6'-trichloro-4,1',6'-trideoxy galactosucrose) which has a sweetness several hundred times that of sucrose. The use of sucralose as a sweetener is disclosed in British Patent Specification No. 1,543,167.

A process for the synthesis of sucralose involving the preparation of 4-PAS and its isomerisation to 6-PAS is disclosed in British Patent Specification No. 2,065,648 B. In this process, 6,1',6'-tri-O-trityl-penta-O-acetyl sucrose ("TRISPA") is detritylated to provide 4-PAS which is then successively isomerised to 6-PAS, chlorinated and deacetylated to yield sucralose.

In a review article on trityl (i.e. triphenylmethyl) ethers of carbohydrates, Helferich (Advances in Carbohydrate Chemistry 3, 79–111, 1948) mentions that trityl ethers can be removed by strong acids in water or organic solvents, or in a mixture of these; by reaction with hydrogen bromide in glacial acetic acid, and by catalytic reduction in the presence of platinum or palladium.

Applying these and similar methods to the selective detritylation of TRISPA, McKeown et al. (Canadian Journal of Chemistry 35, 28–36; 1957), found that (a) reaction with a hydrogen halide in an organic solvent caused extensive inversion of the starting material, (b) catalytic hydrogenation required the use of extremely pure samples of TRISPA to avoid poisoning of the catalyst and, moreover, resulted in low yields of 4-PAS (16 to 38%), and (c) graded hydrolysis with aqueous acetic acid gave 4-PAS conveniently in 43 to 60% yields, with some inversion of the starting material.

In British Patent Specification No. 2,065,648 B it is also disclosed that high yields of 4-PAS (up to 95%) can be obtained simply by treating TRISPA with hydrochloric acid in an inert solvent such as methyl isobutyl ketone in combination with glacial acetic acid (1:1) at a low temperature, e.g. about 0° C. However, the excess of acid in the reaction mixture leads to degradation of 4-PAS and the formation of by-products, and this problem becomes more troublesome when the process is scaled up. Some relief from this problem is obtained by using hydrogen chloride with toluene as the solvent because the product, 4-PAS, separates from solution, leaving most of the trityl chloride which has been generated during the reaction in the mother liquid. Good yields are obtained (around 85%) and the trityl chloride can be recovered and recycled. However, some of the hydrogen chloride and the trityl chloride can become trapped in the product, necessitating lengthy and careful washing to obtain a stable product. In addition, the presence of the highly reactive trityl chloride in the reaction mixture is not conducive to combining the detritylation step with other stages of the process for the preparation of sucralose and therefore it is necessary to isolate and purify the intermediate before proceeding further.

Unexpectedly, we have now found that selective detritylation of TRISPA can be effected by a catalytic process in which a catalytic amount of an aralkyl chloride or hydrogen chloride and a suitable catalyst are added to a solution of TRISPA in an inert organic solvent and the solution is hydrogenated. In this process, a trace of hydrogen chloride is provided, either directly or by hydrogenolysis of the aralkyl chloride, which reacts with the trityl groups of TRISPA to give 4-PAS and trityl chloride which then undergoes hydrogenolysis to release hydrogen chloride, thus completing the cycle.

According to the present invention there is provided a process for the preparation of 2,3,4,3',4'-penta-O-acetyl sucrose (4-PAS), in which a catalytic amount of an aralkyl chloride or hydrogen chloride is added to a solution of TRISPA in an inert organic solvent and the solution is hydrogenated in the presence of a hydrogenolysis catalyst.

In contrast to the known methods of selective detritylation of TRISPA by reaction with an acid, the process of the invention does not involve the use of a large excess of acid and the reaction is carried out under virtually neutral conditions, thus avoiding both degradation of the desired product and the formation of unwanted by-products. It appears that, under the reaction conditions, some of the 4-PAS is isomerised to 6-PAS, so that the product is a mixture of the two, with 4-PAS the major component. However, as the next stage in the sucralose process is the isomerisation to 6-PAS, the presence of some 6-PAS is not at all undesirable.

The catalytic hydrogenolysis can be effected under mild conditions at ambient temperature and at atmospheric pressure, to give 4-PAS in yields of 95% or more. The catalyst is conveniently a form of platinum or palladium, especially on an inert support such as charcoal. The catalyst system of choice is palladium on carbon, in particular a system with about 10% by weight of palladium. The solvent should be an inert solvent which dissolves TRISPA and the aralkyl chloride, and also the reaction products, in order to prevent fouling of the catalyst. Hydrocarbons and halogenated hydrocarbons are of particular use. Halogenated hydrocarbons should be selected among those which are not hydrogenolysed under the conditions used. Esters are also of use. The solvent of choice is dichloromethane, although toluene and ethyl acetate are also of use.

The aralkyl chloride used to initiate the reaction is preferably an arylmethyl chloride, especially a phenylmethyl chloride such as trityl chloride itself or benzyl chloride. Hydrogen chloride itself can be used to initiate the reaction, since the reaction is believed to proceed via hydrogenolysis of the aralkyl chloride to give hydrogen chloride and the aralkane (see below). Only a catalytic amount of the chloride is required, since the hydrogen chloride is consumed and regenerated in the hydrogenolysis reaction. In general about 0.05 to 0.2 mole of chloride per mole of TRISPA is desirable.

Hydrogenolysis of trityl chloride results in the formation of tritane (i.e. triphenylmethane), a stable compound which can be recovered, converted into trityl chloride (e.g. by free-radical chlorination (Kharash et al. J.Amer.Chem. Soc. 1939, 61, 2142) or by conversion into tritanol (Schmidlin et al. Ber., 1912, 45, 3188) followed by chlorination), and recycled to be used in the preparation of 6,1',6'-tri-O-trityl sucrose.

The process is superficially similar to the procedure for catalytic reduction of the trityl groups by hydrogenation of a solution of a trityl ether in the presence of palladium or platinum but, whereas neither we nor McKeown et al, could get this process to work effectively on TRISPA, we have found that the addition of a catalytic amount of trityl chloride to the reaction mixture results in rapid and complete detritylation of TRISPA, with high yields of 4-PAS. While we do not wish to be bound by theoretical considerations, we believe that, in the process of the present invention, hydrogenolysis of trityl chloride (rather than of the trityl groups of TRISPA) occurs and this releases hydrogen chloride which reacts with the trityl groups of TRISPA to yield 4-PAS and more trityl chloride which then undergoes hydrogenolysis to continue the reaction. Tritane accumulates in the reaction mixture but the levels of trityl chloride and of hydrogen chloride remain essentially constant until the detritylation is completed.

Residues of tritane in the reaction mixture do not react with 4-PAS, not do they interfere with the next stage of the process for the preparation of sucralose, i.e. isomerisation of 4-PAS to 6-PAS under acidic (e.g. toluene/acetic acid) or basic (e.g. dichloromethane/tertiary butylamine) conditions. Therefore it is possible to proceed to this stage after most of the tritane has been removed without isolating and purifying the intermediate.

In a further embodiment of the present invention there is provided a process for the preparation of 4-PAS from TRISPA and its isomerisation to 6-PAS under acidic or basic conditions, characterised in that the 4-PAS is prepared by the selective removal of the trityl groups from TRISPA in an inert organic solvent by adding a catalytic amount of an aralkyl chloride or hydrogen chloride and a suitable catalyst to the solution and hydrogenating the solution.

In the final stages of the preparation of sucralose as described in British Patent Specification No. 2,065,648 B, 6-PAS is chlorinated at the 4, 1' and 6' positions to provide 2,3,6,3',4'-penta-O-acetyl sucralose which is then deacetylated to yield sucralose.

In a further embodiment of the present invention there is provided a process for the production of sucralose by the preparation of 4-PAS and its isomerisation to 6-PAS followed by the chlorination of 6-PAS and deacetylation of the sucralose pentaacetate, characterised in that the 4-PAS is prepared by the selective removal of the trityl groups from TRISPA in an inert solvent by adding a catalytic amount of an aralkyl chloride or hydrogen chloride and a suitable catalyst and hydrogenating the solution.

The invention is described further in the following non-limiting Examples.

EXAMPLE 1

Detritylation of TRISPA

To TRISPA (10 g, 95.2% purity, $7.424 \times 10^{-3}$ moles) in dichloromethane (30 ml) was added trityl chloride (0.125 g, $4.488 \times 10^{-4}$ moles) and the solution was hydrogenated at room temperature and at atmospheric pressure in the presence of palladium on charcoal catalyst (10%, 0.1 g). The consumption of gas stopped after 3 molar equivalents had been taken up (reaction time about 3 hr). The hydrogen chloride remaining in the reaction mixture was neutralised with triethylamine (0.05 ml). Examination of the reaction mixture by tlc (silica gel/ethyl acetate) revealed 4-PAS as the major product together with tritane and a little 6-PAS. Removal of the catalyst and solvent and treatment of the residue with toluene (50 ml) overnight afforded a white, crystalline solid which was collected, washed with toluene (5×5 ml) and dried in vacuo at 40°. Yield 4.77 g, 110.4% (4-PAS, 68.3%, 6-PAS, 12.5%; tritane, 2.2%; toluene 8.8% by glc). Yield of total PAS corrected for purity of starting material and product was 93.7%. The mother liquor was concentrated to dryness, and the residue was digested in boiling methanol (25 ml) and set aside overnight to complete the crystallisation. The tritane was collected, washed with methanol (5 ml) and dried in vacuo at 40°. Yield 5.07 g (88.5%) mp 93.5° (lit, 93.4°). Concentration of the filtrate gave a reside (0.74 g) comprising 4-PAS, 8.2%; 6-PAS, 5.0%; tritane, 67.5%; toluene 1.4% (by glc analysis).

EXAMPLE 2

Acetyl Migration of isolated product under acidic conditions

The crude 4-PAS from Example 1 (1.0 g) was dissolved in a warm mixture of toluene (5.0 ml) and acetic acid (0.1 ml) and the solution was heated under reflux for 6 hours (solid began to separate from solution after about 2 hours heating). The mixture was set aside overnight to complete the crystallisation. The product was collected, washed with toluene (2 ml) and dried in vacuo at 50°. Yield 0.779 g, 77.9% (6-PAS, 82.0%, 4-PAS, 2.7%; tritane, 0.7%). Yield corrected for purity of starting material and product was 79.1%. Overall yield corrected for purity of TRISPA was 74.1%.

EXAMPLE 3

Acetyl migration under basic conditions, without isolation

TRISPA (10 g, 95.2% purity) was detritylated as described in Example 1. After neutralization with triethylamine (0.05 ml) and removal of the catalyst the reaction mixture was concentrated under vacuum to contain 10 ml dichloromethane, and tertiary butylamine (0.8 ml) was added. The mixture was heated under reflux for 3 hours and was then concentrated under vacuum to dryness. Treatment of the residue with toluene gave crude 6-PAS (3.3 g) and tritane was recovered from the mother liquor as described in Example 1.

EXAMPLE 4

Preparation of sucralose

To a solution of sulphuryl chloride (15 ml) in 1,2-dichloroethane (15 ml) was added a solution of 6-PAS (5 g, prepared by the procedures of Examples 1 and 2) in pyridine (15 ml) and 1,2-dichloroethane (15 ml) without cooling. The temperature of the mixture rose to about 50° by exothermic reaction and the reaction mixture was heated under reflux for 4 hours, then cooled and dichloroethane (50 ml) added. The resulting solution was washed with 10% hydrochloric acid (100 ml), water and 10% sodium hydrogen carbonate solution to neutralise. The organic phase was dried, concentrated to a syrup in vacuo and crystallised from toluene (25 ml) to give sucralose pentaacetate (4 g). The sucralose pentaacetate was deacetylated with sodium methoxide in methanol in the usual way to give sucralose (2.5 g).

EXAMPLE 5

Conversion of TRISPA into 4-PAS (a) TRISPA (200 g, assay 95% $148.48 \times 10^{-3}$ moles) and trityl chloride (5 g $179.52 \times 10^{-4}$ moles) in dichloromethane (600 ml) was hydrogenated at ambient temperature and atmospheric pressure in the presence of palladium on carbon catalyst (10%, 2.5 g). Uptake of gas was complete in 12 hours and then Amberlite IRA-93(OH) resin (40 g) was added and the suspension was stirred at ambient for 12 hours. Removal of the solids and solvent gave a residue (209 g: assay, 4-PAS 35.1%, 6-PAS 16.7%, tritane 55.5%). Toluene (150 ml) was evaporated from the residue which was then heated with toluene (1000 ml) at 70° for 5 mins. before cooling the mixture to about 15°. The toluene supernatant was decanted from the thick syrup which was then re-extracted with toluene (500 ml) as before. The syrup was passed on to the migration step and the toluene extracts were concentrated to dryness, the residue was digested in hot methanol (500 ml) and the tritane was allowed to crystallise out overnight. Recovered tritane: 103.1 g, 86.7%, m.p. 93°–6°. In a repeat of this experiment the volume of the first toluene extract was reduced to 500 ml and the methanolic mother liquor from the first tritane recovery was used to digest the tritane from the second experiment. This afforded tritane 115.8 g, 97.5%, m.p. 93°–5°.

(b) The syrup from the hydrogenolysis in step (a) was dissolved in toluene (400 ml) and acetic acid (4 ml) and the solution was heated under reflux for 8 hours. The solution was then distilled at atmospheric pressure until a distillate (280 ml) had been collected. Fresh toluene (50 ml) was then added and the mixture was cooled to 20° when it formed a thick suspension which did not stir very well.

To the residue was added triphenylphosphine oxide (16.4 g) and thionyl chloride (41 ml). All of the solids dissolved and the mixture was heated to reflux over 30 minutes and held at reflux for 2 hours. The mixture was then cooled to 0° and water (11 ml) was added followed by methanol (160 ml). Stirring was continued for 1 hour at 0° and then the crude product was collected, washed with cold 10% aqueous methanol (30 ml) and dried in vacuo at 80° to yield 60 g of sucralose pentaacetate. The sucralose pentaacetate was deacetylated with sodium methoxide in methanol in the conventional manner to give sucralose (38 g).

EXAMPLE 6

Use of hydrogen chloride

TRISPA (10 g 95% purity was dissolved in dichloromethane (35 ml) containing dry hydrogen chloride (0.1%). The solution was then shaken with hydrogen in the presence of palladium on carbon catalyst (10%, 125 mg). The consumption of gas stopped after 3 molar equivalents had been taken up (reaction time about 10 hours). The hydrogen chloride remaining was then neutralised with triethylamine and the mixture was worked up as in Example 1 to yield total PAS (4- and 6-) 93.1%.

EXAMPLE 7

Use of benzyl chloride

The procedure of Example 1 was repeated except that benzyl chloride (0.114 g) replaced trityl chloride in the starting solution. The yield of 4-PAS and 6-PAS corrected for purity of starting material and product was 92.8%.

EXAMPLE 8

Use of ethyl acetate as solvent

The procedure of Example 1 was repeated except that ethyl acetate (30 ml) replaced the dichloromethane. The reaction proceeded more slowly, taking about 24 hours. The remaining hydrogen chloride was neutralized and the mixture was worked up, as in Example 1 giving a similar yield of 4-PAS and 6-PAS.

EXAMPLE 9

Use of platinum as catalyst

The procedure of Example 1 was repeated except that platinum on carbon (10%, 0.1 g) was used instead of the palladium. The reaction was complete in about 12 hours. The product was the same as in Example 1.

We claim:

1. A process for the preparation of 2,3,4,3′,4′-penta-O-acetyl sucrose by the selective removal of trityl groups from 6,1′,6′-tri-O-trityl-penta-O-acetyl sucrose (TRISPA), comprising hydrogenating a solution of TRISPA and about 0.05 to 0.2 moles of aralkyl chloride (per mole of TRISPA) in an inert organic solvent in the presence of palladium or platinum as the catalyst.

2. The process of claim 1 wherein the aralkyl chloride is benzyl chloride.

3. The process of claim 1, wherein the aralkyl chloride is trityl chloride.

4. The process of claim 1, wherein the inert organic solvent is a halogenated hydrocarbon.

5. In the process for the preparation of 2,3,6,3′,4′-penta-O-acetyl sucrose (6-PAS) by selective removal of trityl groups from 6,1′,6′-tri-O-trityl-penta-O-acetyl sucrose (TRISPA) to obtain 2,3,4,3′,4′-penta-O-acetyl sucrose (4-PAS) and isomerisation of 4-PAS into 6-PAS by treatment with acid or base, the improvement which comprises the removal of the trityl groups from TRISPA by the hydrogenation of a solution of TRISPA and about 0.05 to 0.2 moles of an aralkyl chloride (per mole of TRISPA) in an inert organic solvent in the presence of palladium or platinum as the catalyst.

6. The process according to claim 5, in which the tritane formed in the hydrogenolysis is removed and the crude 4-PAS is isomerized without first being isolated and purified.

7. The process according to claim 5, wherein the aralkyl chloride is benzyl chloride.

8. The process according to claim 5, wherein the aralkyl chloride is trityl chloride.

9. The process according to claim 5, wherein the inert organic solvent is a halogenated hydrocarbon.

10. In the process for the production of sucralose by selective removal of trityl groups from 6,1′,6′-tri-O-trityl-penta-O-acetyl sucrose (TRISPA) to obtain 2,3,4,3′,4′-penta-O-acetyl sucrose (4-PAS) and isomerisation of 4-PAS into 2,3,6,3′,4′-penta-O-acetyl sucrose (6-PAS) by treatment with acid or base, followed by the chlorination of 6-PAS and deacetylation of the sucralose pentaacetate, the improvement which comprises removal of the trityl groups from TRISPA by hydrogenating a solution of TRISPA and about 0.05 to 0.2 moles of an aralkyl chloride (per mole of TRISPA) in an inert organic solvent in the presence of palladium or platinum as the catalyst.

11. The process of claim 10, wherein the aralkyl chloride is benzyl chloride.

12. The process of claim 10, wherein the aralkyl chloride is trityl chloride.

13. The process of claim 10, wherein the inert organic solvent is a halogenated hydrocarbon.

* * * * *